(12) United States Patent
Lin

(10) Patent No.: US 7,726,873 B2
(45) Date of Patent: Jun. 1, 2010

(54) APPARATUS AND METHOD FOR ANALYZING HEAT-TRANSFERRING FLUID

(75) Inventor: Mong-Tung Lin, Tu-Cheng (TW)

(73) Assignee: Hon Hai Precision Industry Co., Ltd., Tu-Cheng, Taipei Hsien (TW)

( * ) Notice: Subject to any disclaimer, the term of this patent is extended or adjusted under 35 U.S.C. 154(b) by 1027 days.

(21) Appl. No.: 11/450,240

(22) Filed: Jun. 9, 2006

(65) Prior Publication Data

US 2007/0009008 A1 Jan. 11, 2007

(30) Foreign Application Priority Data

Jun. 10, 2005 (CN) .................. 2005 1 0035290

(51) Int. Cl.
*G01N 25/20* (2006.01)
*G01K 17/06* (2006.01)
(52) U.S. Cl. .................. 374/29; 374/44; 374/39; 374/141; 374/31
(58) Field of Classification Search .............. 374/4, 374/29–31, 39–43, 45, 47, 100, 120, 121, 374/130, 135, 141, 147, 165, 27
See application file for complete search history.

(56) References Cited

U.S. PATENT DOCUMENTS

| 6,988,826 B2 * | 1/2006 | Zribi et al. .................. 374/31 |
| 2005/0012069 A1 * | 1/2005 | Maes et al. .................. 252/73 |
| 2007/0261819 A1 * | 11/2007 | Lin .................. 165/80.4 |
| 2009/0296772 A1 * | 12/2009 | Choi et al. .................. 374/43 |

* cited by examiner

*Primary Examiner*—Gail Verbitsky
(74) *Attorney, Agent, or Firm*—Jeffrey T. Knapp

(57) ABSTRACT

An exemplary apparatus (10) is for analyzing a heat-transferring nano-fluid (20) with a view to obtaining information on heat-transferring properties of the nano-fluid. Typically, the nano-fluid is used for heat pipes. The apparatus includes an evaporating device (100) and a detecting device (200). The evaporating device is configured for preparing a gaseous sample (20') of the nano-fluid for analyzing. The evaporating device includes a container (110) configured for containing the nano-fluid, and a temperature controller (120). The container has a first opening (112) allowing vaporized nano-fluid to exit therethrough. The temperature controller is configured for heating the nano-fluid in the container up to a predetermined temperature, and maintaining the nano-fluid at the predetermined temperature. The detecting device is configured for generating a laser light and receiving an optical emission from the gaseous sample, thus enabling heat-transferring properties of the nano-fluid to be analyzed. A related method is also provided.

14 Claims, 2 Drawing Sheets

APPARATUS AND METHOD FOR ANALYZING HEAT-TRANSFERRING FLUID

BACKGROUND

1. Technical Field

The present invention relates to an apparatus and a method for analyzing a heat-transferring fluid with a view to learning about heat-transferring properties of the heat-transferring fluid, and particularly to an apparatus and a method for analyzing a heat-transferring nano-fluid typically used in heat pipes.

2. Related Art

A heat pipe is a heat-transferring mechanism that can transport large quantities of heat between a relatively hot interface and a relatively cold interface where the difference in temperature is very small. A vaporizable liquid is typically employed within the heat pipe for transferring the heat between the hot interface and the cold interface. Nano-fluids that contain nano-particles have been recently developed as an improved kind of heat-transferring fluid. The nano-particles provide the nano-fluid with a thermal conductivity higher than that of a conventional vaporizable liquid. Thus nano-fluids are now commonly employed in place of conventional heat-transferring fluids in the manufacture of heat pipes. It is widely known that adding nano-particles to a base fluid can dramatically increase the heat-transferring properties of the base fluid. However, precisely analyzing the relationship between the quantity and type of nano-particles added and the resulting heat-transferring properties yielded is not easy.

Therefore, what is needed is an apparatus and a method for analyzing a heat-transferring fluid that contains nano-particles, the heat-transferring fluid being typically used for heat pipes.

SUMMARY

In order to analyze a heat-transferring fluid with a view to obtaining information on heat-transferring properties of the heat-transferring fluid, an apparatus adapted for doing so is provided. The heat-transferring fluid contains nano-particles, and is referred to as a nano-fluid. Typically, the heat-transferring fluid is used for heat pipes. The apparatus includes an evaporating device and a detecting device. The evaporating device is configured for preparing a gaseous sample of the heat-transferring fluid for analyzing. The evaporating device includes a container configured for containing the heat-transferring fluid, and a temperature controller. The container has a first opening allowing vaporized heat-transferring fluid to exit therethrough. The temperature controller is configured for heating the heat-transferring fluid in the container up to a predetermined temperature, and maintaining the heat-transferring fluid at the predetermined temperature. At the predetermined temperature, the heat-transferring fluid vaporizes, with the vapor attaining a pressure dynamically balanced with that of ambient air. The detecting device is configured for generating a laser light and receiving an optical emission from the gaseous sample, thus enabling heat-transferring properties of the heat-transferring fluid to be analyzed.

An advantage of the apparatus is that it is easy to handle, accurate, and provides fast data. A related method is also provided herein.

BRIEF DESCRIPTION OF THE DRAWINGS

The above-mentioned and other features and advantages of the present apparatus and method, and the manner of attaining them, will become more apparent and the invention will be better understood by reference to the following description of its embodiments taken in conjunction with the accompanying drawings.

Figure 1:
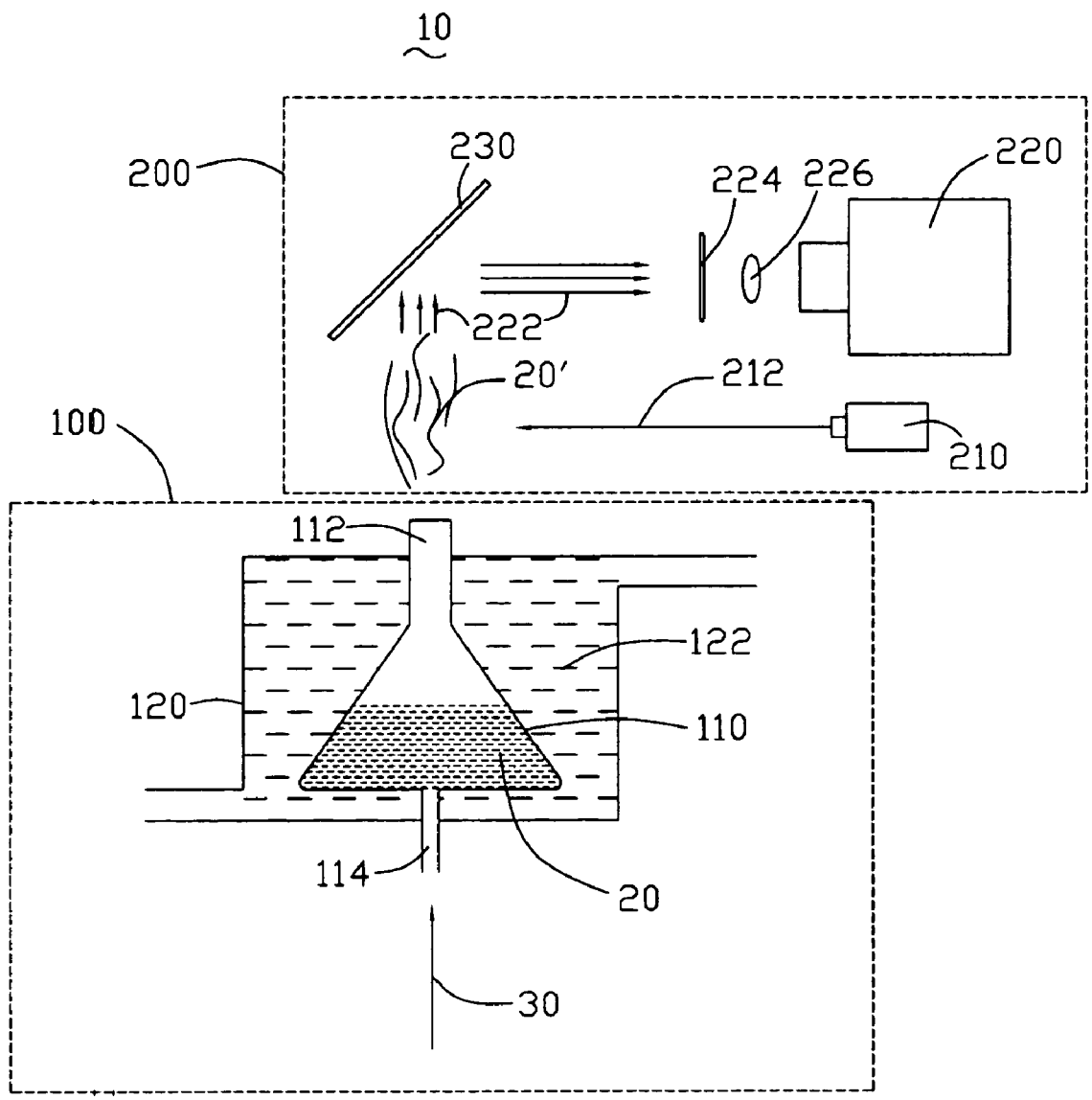
FIG. 1 is a schematic diagram of an apparatus for analyzing a heat-transferring fluid with a view to obtaining information on heat-transferring properties of the heat-transferring fluid, according to an exemplary embodiment of the present invention.

Corresponding reference characters indicate corresponding parts throughout the first drawing. The exemplifications set out herein illustrate at least one preferred embodiment of the present apparatus and method, in one form, and such exemplifications are not to be construed as limiting the scope of such apparatus or method in any manner.

DETAILED DESCRIPTION OF PREFERRED EMBODIMENTS

Reference will now be made to the drawings to describe the preferred embodiments of the present apparatus and method in detail.

Referring to FIG. 1, this shows an apparatus 10 configured for analyzing a heat-transferring fluid 20 containing nano-particles (not shown), with a view to obtaining information on heat-transferring properties of the heat-transferring fluid 20. This kind of heat-transferring fluid 20 is referred to as a nano-fluid. The nano-particles can for example be nano-metal particles, such as nano-copper particles or nano-gold particles, and the heat-transferring fluid 20 is typically employed in heat pipes. However, other nano-particles such as nano-carbon particles that have good thermal conductivity can also be used in connection with the apparatus 10. The apparatus 10 mainly includes an evaporating device 100 configured for preparing a gaseous sample 20' of the heat-transferring fluid 20, and a detecting device 200 configured for detecting photons emitted from the gaseous sample 20'. The detected photons can then be analyzed in order to obtain information on heat-transferring properties of the heat-transferring fluid 20.

The evaporating device 100 includes a container 110 and a temperature controller 120. The container 110 is configured for containing the heat-transferring fluid 20 to be analyzed. The container 110 includes at least a first opening 112 for allowing the gaseous sample 20' to escape upwardly therefrom. The temperature controller 120 is configured for maintaining the heat-transferring fluid 20 in the container 110 at a predetermined temperature. At the predetermined temperature, the heat-transferring fluid 20 vaporizes, with the vapor attaining a pressure greater than that of ambient air. Thereby, the vaporized heat-transferring fluid 20 exits the first opening 112 and generates the gaseous sample 20' thereat.

It is to be noted that in general, different heat-transferring fluids have different liquid-gas phase conversion points. The quantity and kind of nano-particles added in a base fluid also changes the phase conversion point of the base fluid. Accordingly, the predetermined temperature referred to above is preferably determined according to the practical liquid-gas phase conversion point of a base fluid comprised in the heat-transferring fluid, and according to the quantity and kind of nano-particles used in the base fluid.

According to another embodiment of the apparatus 10, the container 110 further includes a second opening 114. The second opening 114 is provided at a bottom of the container 110, for allowing a carrier gas 30 to be inputted therethrough into the container 110. In this embodiment, the above-mentioned predetermined temperature may be lowered somewhat, depending on an amount of extra pressure that is introduced by inputting the carrier gas 30.

The temperature controller 120 includes a liquid bath device. Preferably, the liquid bath device is a hot water bath device including hot water 122 therein. The container 110 is set in the hot water bath, so the heat-transferring fluid 20 in the container 110 is surrounded by the hot water 122 and can exchange heat with the hot water 122.

The detecting device 200 includes a laser light source 210 and a photon detector. In the exemplary embodiment, the photon detector is an optical emission detector 220. The laser light source 210 is configured for providing a laser light 212 that illuminates the gaseous sample 20' located over the first opening 112 of the container 110. The optical emission detector 220 is configured for detecting and receiving photons emitted from the gaseous sample 20' when the gaseous sample 20' is illuminated by the laser light 212. In the exemplary embodiment, the photons constitute an optical emission 222.

According to another embodiment of the apparatus 10, the apparatus 10 further includes a guiding means 230 such as a reflecting mirror. The guiding means 230 is configured for directing the optical emission 222 from the gaseous sample 20' to the optical emission detector 220. The apparatus 10 preferably further includes a filter 224 positioned in a path of the optical emission 222 immediately in front of the optical emission detector 220, for reducing or eliminating any possible optical noise emissions included in the optical emission 222.

According to one embodiment of the apparatus 10, the optical emission detector 220 includes a charge coupled device (CCD) or a complementary metal oxide semiconductor (CMOS) device. The optical emission detector 220 can alternatively further include a converging lens 226, which positioned in a path of the optical emission 222 adjacent to the filter 224. The converging lens 226 is configured for collecting more optical emissions 222, and thereby improving a sensitivity of the optical emission detector 220.

Figure 2:
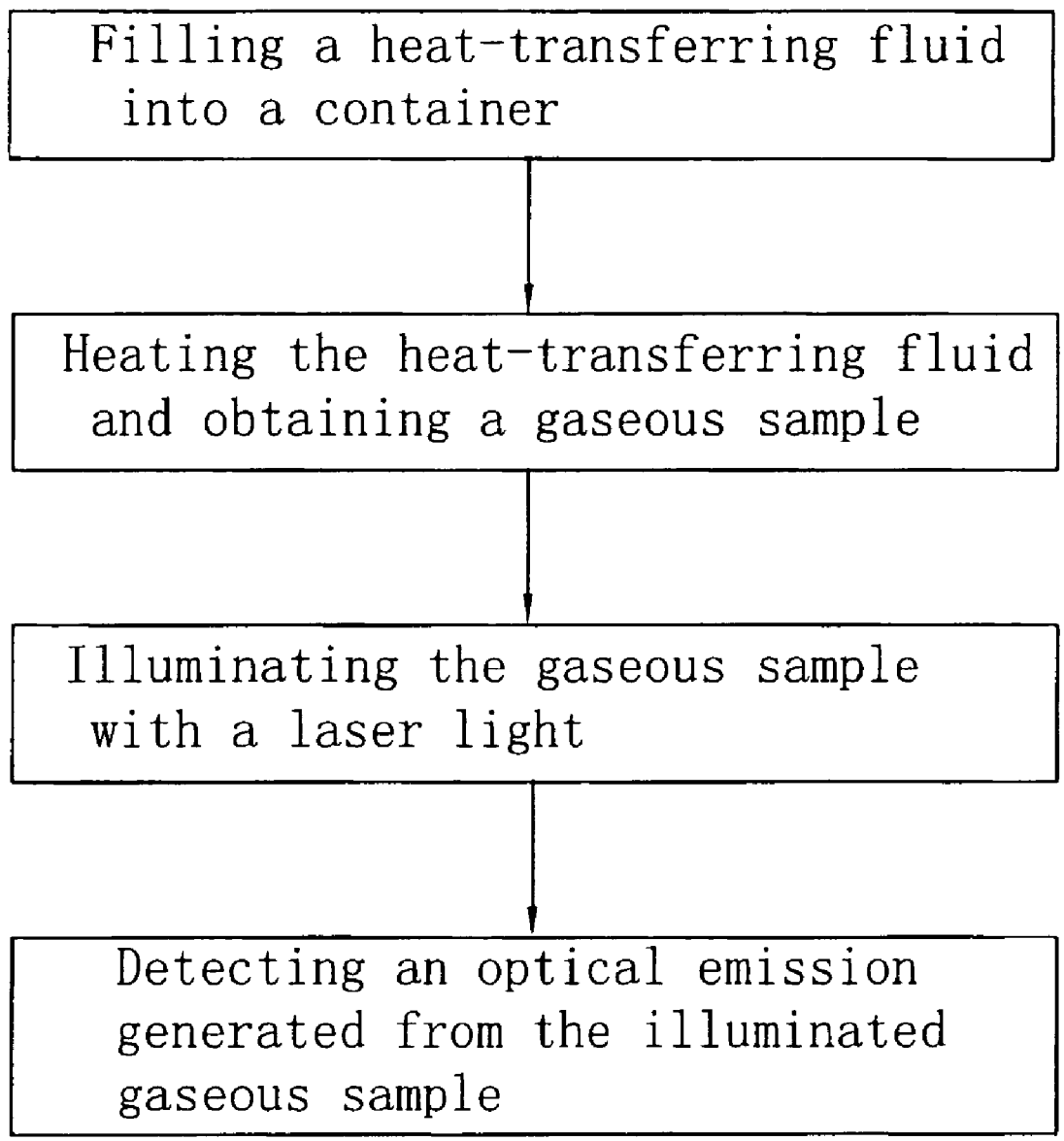
FIG. 2 is a flowchart of a method for analyzing a heat-transferring fluid with a view to obtaining information on heat-transferring properties of the heat-transferring fluid, according to another exemplary embodiment of the present invention.

FIG. 2 is a flowchart of a method for analyzing a heat-transferring fluid, with a view to obtaining information on heat-transferring properties of the heat-transferring fluid, according to an exemplary embodiment of the present invention. The method is typically performed using the above-described apparatus 10.

Referring also to FIG. 1, the method will be described in relation to analyzing the heat-transferring fluid 20. The method mainly includes the following steps. Firstly, the heat-transferring fluid 20 is filled into the container 110 having the first opening 112. Secondly, the heat-transferring fluid 20 is heated by the hot water bath 120 up to and stably maintained at a predetermined temperature, which is equal to a liquid-gas phase conversion point of the heat-transferring fluid 20. At such temperature, the heat-transferring fluid 20 is vaporized, and the vaporized heat-transferring fluid 20 exits the first opening 112 and thus provides the gaseous sample 20'. Thirdly, the laser light 212 illuminates the gaseous sample 20' over the first opening 112, and atoms of the gaseous sample 20' emit photons. In an exemplary embodiment, the photons constitute the optical emission 222. The optical emission 222 can be considered to contain information on the heat-transferring properties of the heat-transferring fluid 20. Finally, the optical emission 222 is detected by an photon detector. In an exemplary embodiment, the photon detector is the optical emission detector 220. The results of detection can then be analyzed to obtain information on the heat-transferring properties of the heat-transferring fluid 20.

According to another embodiment, the method further includes inputting the carrier gas 30 through the second opening 114 at the bottom of the container 110, for facilitating vaporization of the heat-transferring fluid 20. The carrier gas 30 is preferably selected from the group consisting of nitrogen, argon, helium, neon, krypton, and xenon. In this embodiment, the above-described predetermined temperature may be equal to or lower than the liquid-gas phase conversion point of the heat-transferring fluid 20.

A more detailed exemplary embodiment of the method for analyzing a heat-transferring fluid is as follows. In carrying out the method, the above-described apparatus 10 can be utilized under normal room temperature and pressure conditions. The heat-transferring fluid 20 is prepared and filled in the container 10. Then the thermal controller 120 is activated to heat the container 110 and the heat-transferring fluid 20 contained therein up to a predetermined temperature. In this exemplary embodiment, the predetermined temperature is slightly lower than a liquid-gas phase conversion point of the heat-transferring fluid 20. After the heat-transferring fluid 20 has been stably maintained at the predetermined temperature, a carrier gas 30 is inputted into the container 110 through the second opening 114 thereof. The carrier gas 114 is preferably nitrogen, which is relatively inexpensive. However, other gases such as argon, helium, neon, krypton, or xenon may be employed as the carrier gas 30. The heat-transferring fluid 20 is thus vaporized, and a mixture of the carrier gas 30 and the vaporized heat-transferring fluid 20 moves toward the first opening 112. The vaporized heat-transferring fluid 20 exits the first opening 112 and provides the gaseous sample 20' of the heat-transferring fluid 20 thereat.

The laser light source 210 generates a laser light 212 to illuminate the gaseous sample 20'. When illuminated by the laser light 212, unsaturated outer-shell electrons of atoms contained in the gaseous sample 20' absorb photons of the laser light 212, and are excited to jump from a basic level of energy to a higher metastable level of energy. The outer-shell electrons cannot remain at the metastable level for long. When any outer-shell electron jumps back to the basic level, a photon having an energy that is the difference between the basic level of energy and the metastable level of energy is emitted. Such a photon is considered as containing information related to the physical properties of the matter which emitted the photon. For example, different atoms emit photons of different wavelengths. A plurality of emitted photons constitutes the optical emission 222, which is reflected by the guiding means 230 to the optical emission detector 220. By performing appropriate analysis of the optical emission 222 collected by the optical emission detector 220, heat-transferring properties of the heat-transferring fluid 20 can be obtained.

While the invention has been described as having preferred and exemplary embodiments, further modifications within the spirit and scope of this disclosure are intended to be included. This disclosure is intended to cover any variations, uses, or adaptations of the invention using its general principles. Further, this disclosure is intended to cover such departures from the described embodiments as come within known or customary practice in the art to which this invention pertains and which fall within the limits of the appended claims or equivalents thereof.

What is claimed is:

1. An apparatus for analyzing a heat-transferring fluid containing nano-particles with a view to obtaining information on heat-transferring properties of the heat-transferring fluid, the apparatus comprising:
   an evaporating device configured for preparing a gaseous sample of the heat-transferring fluid for analysis, the evaporating device comprising:
      a container configured for containing the heat-transferring fluid, the container comprising a first opening configured for allowing vaporized heat-transferring fluid to exit therethrough; and
      a temperature controller configured for heating the heat-transferring fluid in the container up to a predetermined temperature and maintaining the heat-transferring fluid at the predetermined temperature; and
   a detecting device configured for detecting an optical emission generated from the vaporized heat-transferring fluid.

2. The apparatus as described in claim 1, wherein the detecting device comprises:
   a laser light source configured for providing a laser light illuminating the gaseous sample over the first opening of the container and thereby generating the optical emission; and
   an optical emission detector configured for receiving and detecting the optical emission.

3. The apparatus as described in claim 2, wherein the detecting device further comprising a guiding means configured for directing the optical emission to the optical emission detector.

4. The apparatus as described in claim 2, wherein the detecting device further comprises a filter positioned in a path of the optical emission immediately in front of the optical emission detector, and configured for reducing or eliminating potential noise emissions.

5. The apparatus as described in claim 3, wherein the guiding means is a reflecting mirror that reflects the optical emission to the optical emission detector.

6. The apparatus as described in claim 2, wherein the optical emission detector comprises a charge coupled device or a complementary metal oxide semiconductor device.

7. The apparatus as described in claim 1, wherein the container further comprises a second opening at a bottom thereof configured for allowing a carrier gas to be inputted therethrough.

8. The apparatus as described in claim 1, wherein the temperature controller comprises a liquid bath device.

9. A method for analyzing a heat-transferring fluid containing nano-particles with a view to obtaining information on heat-transferring properties of the heat-transferring fluid, the method comprising:
   filling the heat-transferring fluid into a container that includes a first opening;
   heating the heat-transferring fluid up to a predetermined temperature and stably maintaining the heat-transferring fluid at the predetermined temperature, wherein at the predetermined temperature, the heat-transferring fluid is vaporized, and the vapor exits the first opening and provides a gaseous sample;
   illuminating the gaseous sample with a laser light; and
   detecting an optical emission generated from the illuminated gaseous sample.

10. The method as described in claim 9, wherein a hot water bath device is employed for heating the heat-transferring fluid up to the predetermined temperature and maintaining the heat-transferring fluid at the predetermined temperature.

11. The method as described in claim 9 further comprising inputting a carrier gas through a second opening of the container, for facilitating vaporization of the heat-transferring fluid and movement of the vaporized heat-transferring fluid to exit the first opening.

12. The method as described in claim 11, wherein the second opening is provided at a bottom of the container.

13. The method as described in claim 11, wherein the carrier gas is selected from the group consisting of nitrogen, argon, helium, neon, krypton, and xenon.

14. The method as described in claim 9, wherein the predetermined temperature is equal to or lower than a liquid-gas phase conversion point of the heat-transferring fluid.

* * * * *